United States Patent [19]

Hrynewycz

[11] 4,262,824

[45] Apr. 21, 1981

[54] LOW-CURRENT E-FRAME ELECTRONIC MAGNET WITH A PERMANENT MAGNET ARMATURE FOR AN I. V. VALVING CONTROLLER

[75] Inventor: Orest Hrynewycz, Elmwood Park, Ill.

[73] Assignee: Baxter Travenol Laboratories, Inc., Deerfield, Ill.

[21] Appl. No.: 120,234

[22] Filed: Feb. 11, 1980

Related U.S. Application Data

[63] Continuation of Ser. No. 878,650, Feb. 17, 1978, abandoned.

[51] Int. Cl.³ .............................................. A61M 5/14
[52] U.S. Cl. .................................. 222/450; 222/504; 335/179; 335/234; 128/214 R
[58] Field of Search ................ 335/79, 179, 234, 266, 335/268; 251/65; 128/214 R, 214 C, 214.2, 227; 222/206, 207, 212, 214, 447, 450, 452, 445, 449, 504

[56] References Cited

U.S. PATENT DOCUMENTS

| | | | |
|---|---|---|---|
| 2,407,418 | 9/1946 | Hanff | 335/234 |
| 2,896,132 | 7/1959 | Sauer | 335/234 |
| 3,027,499 | 3/1962 | Holdway | 335/234 |
| 3,673,529 | 6/1972 | Garratt et al. | 335/234 |
| 4,121,584 | 10/1978 | Turner et al. | 128/227 X |

FOREIGN PATENT DOCUMENTS 155233 12/1963 U.S.S.R. .................................. 335/179

Primary Examiner—David A. Scherbel
Attorney, Agent, or Firm—Paul C. Flattery; John P. Kirby, Jr.; Garrettson Ellis

[57] ABSTRACT

A pivoting permanent-magnet armature of an electromagnet forming part of a controller to limit the flow of an intravenous solution through a casette to a patient. The electromagnet may have an E-frame with the permanent magnet pivoting between two positions about a point lying on the extension of the electromagnet's middle leg. In one position, one pole of the permanent magent contacts one side leg of the E-frame to open the casette inlet and maintain the outlet in a closed configuration. In the other position, the permanent magnet's other pole contacts the other side of the E-frame to close the inlet, open the outlet, and allow fluid to flow to the patient. A gap should remain between the permanent magnet and the E-frame's middle leg to avoid their grinding together and a concomitant increase of friction due to the presence of resulting particles. Preventing contact between the permanent magnet and the electromagnet's middle leg also avoids the formation of the magnetic shunt between the two at that point. This has particular importance when the armature assumes the form of a rocker arm with two separate permanent magnets attached at its ends. A strip of plastic attached to either the middle leg of the E-frame or to the rocker-arm armature achieves the magnetic separation of the components but then allows mechanical contact to stabilize their operation.

12 Claims, 4 Drawing Figures

U.S. Patent  Apr. 21, 1981  4,262,824

LOW-CURRENT E-FRAME ELECTRONIC MAGNET WITH A PERMANENT MAGNET ARMATURE FOR AN I. V. VALVING CONTROLLER

CROSS-REFERENCES TO RELATED APPLICATIONS

This application is a continuation of Application Ser. No. 878,650, filed Feb. 17, 1978 of Orest Hrynewycz, entitled: "LOW-CURRENT E-FRAME ELECTRONIC MAGNET WITH A PERMANENT MAGMET ARMATURE FOR AN I.V. VALVING CONTROLLER", now abandoned.

The controller discussed in the subject application may make use of the Z-shaped bracket shown in the design patent application of Nick Zissimopoulous entitled: "CASSET HOLDER AND TRANSPORTER IN A FLUID FLOW LIMITING DEVICE", U.S. Application Ser. No. 878,965, filed Feb. 17, 1978, now abandoned. It may also utilize the mechanical components disclosed in the pending patent application "IMPROVED FLUID-FLOW LIMITING APPARATUS FOR USE WITH INTRAVENOUS SOLUTION ADMINISTERING EQUIPMENT" of Nick Zissimopoulous, Application Ser. No. 878,970, filed Feb. 17, 1978, now U.S. Pat. No. 4,185,759; the electronic circuitry of the pending patent application "DIGITAL ELECTRONICS AND CASETTE SIZE FOR INTRAVENOUS FLUID-FLOW LIMITING EQUIPMENT" of Vincent L. Knigge and Norman Shim, Ser. No. 878,846, filed Feb. 17, 1978, now U.S. Pat. No. 4,205,238; and either of the electromagnet shapes displayed in the design patent applications "E-FRAME ELECTROMAGNET HAVING A PERMANENT MAGNET ROCKER-ARM ARMATURE" of Orest Hrynewycz, U.S. Application Ser. No. 878,649, filed Feb. 17, 1978 and now abandoned; and "E-FRAME ELECTROMAGNET HAVING PERMANENT MAGNETS ATTACHED TO A ROCKER-ARM ARMATURE" of Nick Zissimopoulous, Application Ser. No. 878,832, filed Feb. 17, 1978 and now abandoned. In addition to aspects of the above applications, the casette in the subject application may utilize a structure including the elastomeric membrane discussed in the pending patent application "CASETTE FOR USE WITH AN I.V. INFUSION CONTROLLER" of Scott T. Garrett, Lee K. Kulle, and William L. Rudenza, Application Ser. No. 878,966, filed Feb. 17, 1978, now U.S. Pat. No. 4,181,245; the valving configurations of the pending patent application "NON-CRITICALLY ALIGNED VALVING DEVICES FOR FLOW RATE LIMITING CASETTE USED IN INTRAVENOUS SOLUTION ADMINISTERING EQUIPMENT" of Scott T. Garrett, Thurman S. Jess, Vincent L. Knigge, Lee K. Kulle, William L. Rudzena and Nick Zissimopoulous, U.S. Application Ser. No. 878,847 filed Feb. 17, 1978, now U.S. Pat. No. 4,223,813; and the shape shown in the design patent application "VALVABLE CASETTE" of Lee K. Kulle and William L. Rudzena, Ser. No. 878,962, filed Feb. 17, 1978, and now abandoned. All of these referenced applications have the same filing date as the subject application.

BACKGROUND

During the administration of an intravenous solution, the flow rate of the liquid to the patient must remain below that level which can needlessly injure him. Frequently, the solution includes a medication. An unacceptably high flow rate can produce excessive concentrations of the medication at different points in the patient's body. The medication, not properly diluted, can then act as a toxic chemical and have a destructive effect upon the tissues of the patient's system.

Even where the solution contains no ingredient other than the usual salts and nutrients, its flow rate must also remain at a safe level. Increasing the flow rate beyond that point allows the intravenous solution to significantly thin the patient's blood. The tissues dependent upon the blood stream for their support may not, when required, receive an adequate supply of the biochemicals entrained in the blood stream. Thus, they could undergo significant damage even though the intravenous solution itself contains only benevolent ingredients.

Various components of a system to limit the flow rate of intravenous solutions to a patient received discussion in the patent applications listed above. The system first includes a casette which forms part of the actual conduit transporting the solution to the patient. It has a metering chamber formed partially of an elastomeric membrane but with a predetermined maximum volume. An inlet and an outlet provide a fluid path for the solution into and out of the metering chamber. A cover slip of plastic limits the membrane's expansion as fluid enters the metering chamber.

To control the flow of fluid into and out of the casette's metering chamber, the system also provides a controller which attaches onto the casette. Two valving members, or rods, pass through the cover slip to open and close, sequentially, the casette's inlet and outlet. To do so, each deforms a portion of the elastomeric membrane in the region of the appropriate valve to block the passage of fluid through it.

A cycle of operation begins with the opening of the casette's inlet and the closing of its outlet. Fluid, under the influence of gravity, flows into the metering chamber until the membrane has reached its largest size. At that point, the chamber contains its predetermined maximum volume.

The inlet closes and immediately afterwards the outlet opens. Fluid from the metering chamber then passes along the conduit and to the patient. After the metering chamber has emptied, the outlet closes with the subsequent opening of the inlet to begin a new cycle. The frequency with which the controller provides the cycles of operation determines the rate of flow of solution to a patient. Switches provided on the controller allow the attendant to vary, within limits, the frequency of the operational cycles and, thus, to change the amount of fluid passing to the patient.

The valving rods, in turn, couple to a rocker arm which constitutes the armature of an E-frame electromagnet. The rocker arm has small permanent magnets glued to its ends. The arm pivots about a point located approximately midway between these magnets and on a line passing lengthwise through the middle leg of the E-frame. The rocker arm pivots between two stable configurations. In the first, the magnet at one of the arm's ends contacts one of the E-frame's side legs while the other ends remain spatially separated from each other. When the rocker arm pivots to its other stable configuration, the second magnet makes contact with the other side leg of the E-frame while the first magnet and the first leg no longer do so.

In one of its configuration, the rocker arm extends the outlet valve member to close the casette's outlet while it retracts the inlet valve member to open the inlet. The metering chamber then fills with intravenous solution. In the second position, the rocker arm opens the outlet and closes the inlet. The fluid that previously filled the metering chamber can then flow to the patient.

The couplings between the rocker arm and the valve members display an appreciable degree of springiness. As a result, the rocker arm, as it pivots between its two positions, maintains the closed valve in that configuration while it forces the other valve member to close the second valve. As the rocker arm continues to pivot, the first valve opens but only after the second valve closes. This "make-before-break" sequence of events provides assurance that both valves on the casette cannot remain open at the same time. This avoids any period of time during which fluid could flow through the casette in an uncontrolled manner.

Electronic circuitry within the controller connects to a coil which surrounds the E-frame's middle leg. Current flowing in a first direction causes both side legs of the E-frame to become magnetic poles of the same type; in other words, both will either become North or both will become South poles. The permanent magnets on the rocker arm, however, project different magnetic poles to the E-frame. Thus, the E-frame, by attracting one of the permanent magnets and repelling the other, places the rocker arm in the desired position. Reversing the current, the coil causes the side legs to both become the other type of magnetic pole. The rocker arm consequently, switches between its two stable positions.

The electronic circuitry within the controller translates the selection of the desired flow rate into the appropriate pulses of current to the coil on the E-frame's middle leg. These current transients place the rocker arm in the required positions for the appropriate lengths of time.

The system including the casette and the controller displays many advantages. These includes the minimal weight inhering in the controller itself. Thus, the controller may simply attach to a casette interposed within the usual flow path of the intravenous solution. It needs no table or shelf on which to sit.

Furthermore, the controller undergoes minimal movement in providing the required management of the casette, especially its valves. At the end of the appropriate time intervals, the rocker arm slightly pviots from one of its stable positions to the other to change the casette's valving configurations. Until the end of the following time interval, it need not and, in fact, cannot undergo further motion. Thus, the controller requires minimal energy to function properly. It consequently may use, as a source of its energy, a small battery, such as those seen in transitor radios.

The amount of force required to move the rocker arm, however, determines the energy drain on the battery powering the controller in its normal operations. Facilitating the rocker arm's changes of position portends the further reduction of the controller's energy requirement and the concommittant increase in the life of its battery.

Operating on battery current greatly expands the utility of the controller and casette system. It allows their use under situations not providing access to a constant supply of electricity. Thus, it can function at the scenes of accidents or other traumatic occurrences and also in buildings while a patient moves from one location to another.

SUMMARY

Providing an electromagnet requiring less power to function can effect substantial savings in the energy it uses. Employing a single rigid permanent magnet as the rocker arm helps achieve this objective. So does maintaining a spatial separation between the rocker arm and an E-frame's middle leg.

Broadly speaking, the casette has a metering means, or chamber, which holds a predetermined volume of fluid. A closable inlet, in fluid communication with the metering chamber, permits the flow into it of fluid. A closable outlet, also in fluid communication with the metering chamber, allows the fluids egress.

To operate the casette, the controller has first and second rigid valving members, with each movable between two positions. Each can occupy one position where it closes its appropriate opening.

The controller further includes an actuating device, connectable to and operatable upon a source of power. It functions by selectively either moving the first valving member to the position where it can close the inlet or moving the second valving member to where it closes the outlet.

Should the source of power fail, the controller should prevent the uncontrolled passage of intravenous solution to the recipient. Convenient components for achieving this objective include a bistable magnetic device which, in the absence of power, moves one of the valving members into the position where it will close its corresponding valve.

This controller can operate with efficiency and require little power where the bistable magnetic device includes a permanent magnet in the form of an elongated rigid member. The magnet should have its magnetic poles near the member's ends. To achieve the bistable condition, the poles of the magnetic should lie in proximity to ferromagnetic material. Yet, the magnet should remain pivotable relative to it in order to move between two stable configurations. The pivot point should generally fall on a first line perpendicularly bisecting a second line which extends between the magnetic poles of the permanent magnet.

The ferromagnetic material may most conveniently take the form of an electromagnet. With an associated coil to induce magnetization, the electromagnet may provide the motive force to move the permanent magnet between its two stable configurations. Concommittantly, the electromagnet achieves the valving configuration required to operate the casette. In this form, the ferromagnetic material represents part of both the controller's bistable magnetic device and its actuating device.

An E-frame electromagnet having the coil wrapped around its middle leg efficiently provides the magnetic fields required to pivot the permanent magnet about its axis of rotation. If current flows in either direction in the coil, the ends of the side legs always produce the same type of magnetic pole. When the current flows in a first direction, the electromagnet's side legs will both produce North poles, for example. When this happens, the North pole on one side leg will attract the South pole of the permanent magnet, while the North pole on the other side leg must repel the North pole of the permanent magnet. These two forces pivot the permanent magnet to one of its two stable configurations. Reversing the current produces the other, or South pole, at the two side legs. The side leg opposite the North magnet pole would attract it while the South magnetic field at the other side leg would repel the permanent magnet South pole. This second set of forces would cause the permanent magnet to pivot until its North pole touches the side leg adjacent to it. The valving configuration in the casette, would, as a consequence, undergo a change. Employing other terms, the controller may have a magnetic actuating device which can connect to and operate upon a source of electric current. This magnetic device functions by selectively moving either of the two valving members to their positions where they can close their respective valves.

Under these circumstances, the magnetic actuating device includes a permanent magnet coupled to the valving members. The magnet again assumes the form of an elongated rigid member having its magnetic poles near its ends. An electromagnet having its poles located near the poles of the permanent magnet includes a coil which connects to the source of electric current. The coil selectively induces the two poles of the electric magnet to both become magnetic poles of a first type and then to both become magnetic poles of the other type. In reaction, the permanent magnet pivots relative to the electromagnet on the line perpendicularly bisecting the connecting line extending between the former's two magnetic poles.

The controller need not utilize a permanent magnet as its rocker arm in order to benefit from an E-frame electromagnet. Regardless of its nature, however, a rocker arm used with this type of electromagnet should, however, not make direct contact with the E-frame's middle leg. To prevent it, the controller includes a structure, coupled at least to the rocker arm or to the E-frame, for spatially removing the rocker arm from the E-frame's middle leg. In other words, the ferromagnetic material forming the middle leg of the E-frame should not contact the ferromagnetic material of the permanent magnet. The two components will not then rub against each other and frictionally oppose the efforts of the magnet to change the rocker arm's orientation. Moreover, without their grinding together, they will not produce filings which even further increases the current drain on the battery required to power the rocker arm between its positions.

Additionally, actual contact between the components can create a magnetic shunt between the middle of the rocker arm and the E-frame's middle leg. This reduces the magnetic field strength at between both side legs of the electromagnet and the magnetic poles at the ends of the rocker arm. This would rob the battery of current not having a productive use.

The space between the rocker arm and the E-frame's middle leg may simply take the form of an air gap. However, a plastic material may fill that space. When that occurs, it provides mechanical rigidity between the two components while avoiding the significant detriments of magnetic contact between them.

DETAILED DESCRIPTION

Figures 1, 2, 3, 4:
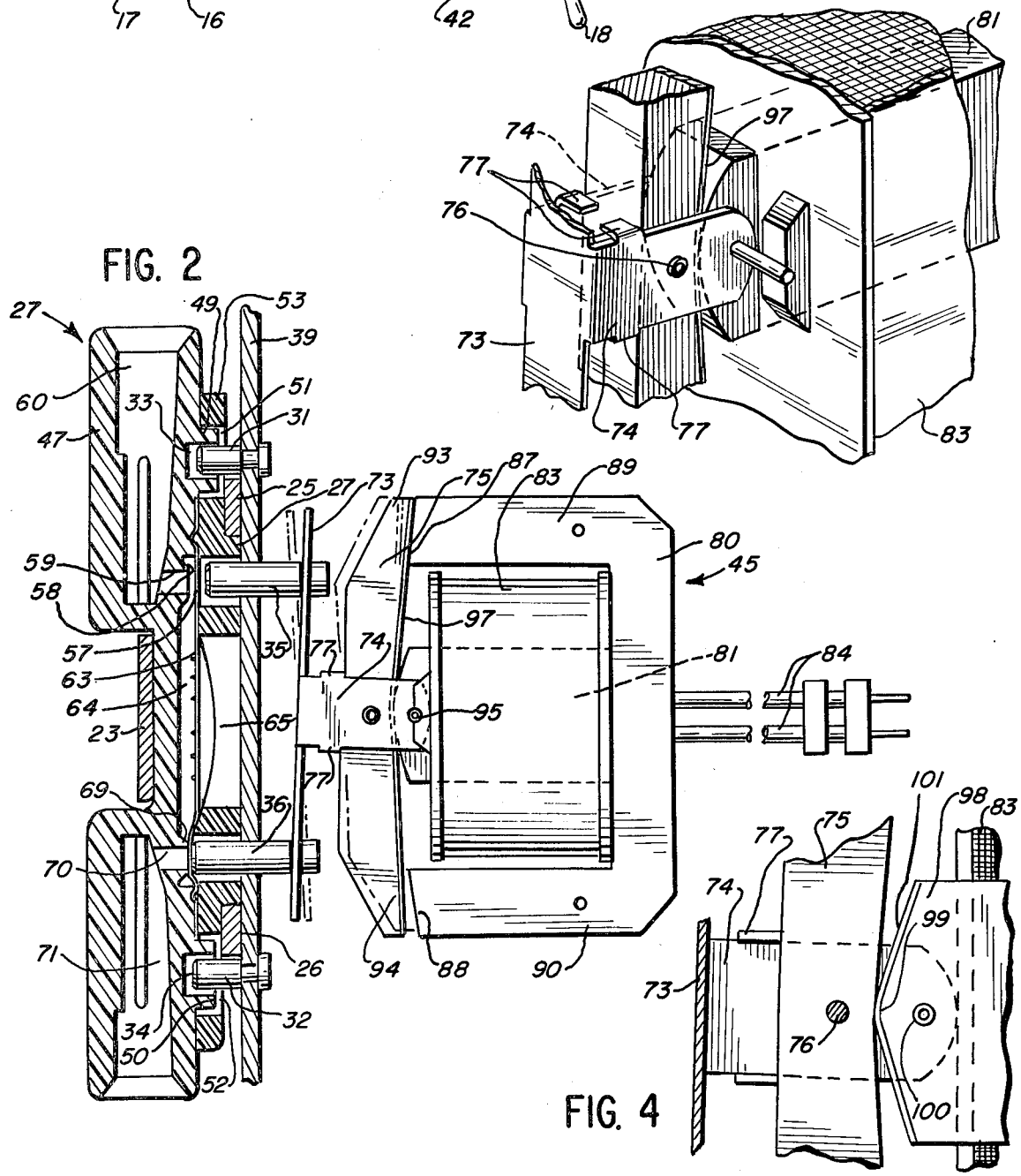
FIG. 1 gives a top plan view, partly in cross section, of a controller providing timed valving action for a casette forming part of the fluid path of an intravenous solution administered to a patient.
FIG. 2 shows, in a front elevational view, the electromagnet of FIG. 1 providing valving action for a casette shown in cross section.
FIG. 3 has a perspective enlarged view of the region of the rocker arm and middle leg of the E-frame of FIG. 2 showing their pivotal connection.
FIG. 4 gives a side elevational view of a modified connection between a rocker arm and the middle leg of an E-frame electromagnet.

The controller, indicated generally at 10 in FIG. 1, includes the back panel 11 and the case having the top 12, the bottom 13, the sides 14 and 15, and the front 16. The rotary thumb switches 17 generally permit the choice of the desired number of milliliters per hour, for example, of intravenous solution that should flow to the patient. The actual digits selected appear through an opening in the front 16. The on-off switch 18 also projects through the front 16 and either permits or disallows the functioning of the controller 10. The front panel also displays a low-battery indicator which does not appear in the view of FIG. 1.

To permit its engagement with the controller 10, a casette enters the opening 21 in the front 16. More accurately, the opposite usually occurs. Typically, the casette forms part of the fluid flow path from the bottle of solution to the patient. It attaches to the bottle which hangs from a suitable supporting rod. The controller then attaches to the casette. In fact, it receives its sole support from the casette to which it attaches. Consequently, the attendant places the controller around the casette, with the casette entering through the opening 21 in the front panel 16.

As the casette enters the opening 21, it passes between the plate 23 and the arms 25 and 26 (with the latter appearing in FIG. 2). The arms 25 and 26 serve to orient the casette in the vertical direction within the controller 10. They surround a protuberance 27, shown in FIG. 2, on the casette 28 to do so. The plate 23 and the arms 25 and 26 form part of an integral metal holder which attaches to the casette.

When the casette engages these components, the attendant turns the knob 29 to the right in FIG. 1. This rotates the shaft 30 in the same direction which, concommittently, moves the holder formed of the plate 23 and the arms 25 and 26 to the right. The casette 27, retained by these components, consequently, moves to the right (or, the controller 10 moves to the left relative to the casette).

As the casette moves to the right, the alignment pins 31 and 32 enter the openings 33 and 34 in the casette 27 of FIG. 2. This aligns the casette 27 relative to the valving members 35 and 36, discussed below.

The alignment pins 31 and 32 attach to the middle leg 39 of the Z bracket 40. The long screws 41 and the short screws 42, in turn, attach the Z bracket 40 to the controller's front 16. The Z bracket 40 also provides support for the shaft 30, the metal holder including the plate 23 and the arms 25 and 26, and the electromagnet indicated generally at 45.

As seen in FIG. 2, the opening 33 in the casette 27 snugly fits around the alignment pin 31. However, the opening 34 has an elongated shape with its longer dimension oriented towards the other opening 33. The snug fit of the opening 33 around its pin 31 and the contact of the sides of the opening 34, with the alignment pin 32 assures the unique and proper alignment of the casette 27 into the controller 10. The elongated shape of the opening 34 simply provides the manufacturing process with some tolerance with regards to its location.

The openings 33 and 34 appear in the base section of plastic 47. Furthermore, the base plastic section 47 has the protuberances 49 and 50 which surround the openings 33 and 34. These protuberances 49 and 50, in turn, fit into the openings 51 and 52 in a cover plastic section 53. The insertion of the former into the latter properly aligns the cover plastic slip 53 relative to the base plastic section 47. Again, the opening 52 has an elongated shape and allows some degree of manufacturing tolerance to the cover slip 53. The opening 51, however, fits snugly around the protuberance 49 and uniquely orients the two plastic sections 47 and 53 of the casette 27 relative to each other.

The controller 10 and the casette 27 operate in cycles to provide a limited flow rate of an intravenous solution to a patient. To begin a cycle of operation, the inlet valve member 35 occupies its retracted position, shown in FIG. 2. There, it permits the elastomeric member 57 to contract to its flat configuration and occupy an position removed from the valve face 58 of the inlet 59. As a result, fluid may flow from the inlet channel 60, which connects to the bottle of solution, through the inlet 59. It then passes to the metering chamber 63 located between the membrane 57 and the plastic back 64 of the base section of plastic 27.

As the fluid enters the metering chamber 63, it forces the membrane 57 to expand into a rounded shape until the latter reaches the concave depression 65 formed in the cover plastic slip 53. At that point, the metering chamber holds its maximum volume of fluid and can accept no more. After this, the inlet valve 35 presses the membrane 57 against the inlet valve face 58 to close the inlet 59. The outlet valve member 36, subsequently, retracts and allows the membrane 57 to move away from the valve face 69 of the outlet 70. The fluid from the metering chamber 63 may then flow out the outlet 70 and the outlet channel 71 and to the patient.

The valving members 35 and 36 connect to the spring link 73. The ends of the link 73 have slots which fit into grooves provided at the ends of the valving members 35 and 36. When the inlet valving member 35 has opened the inlet 59 and the outlet valving member 36 has closed the outlet 70, the spring link occupies the position shown in solid lines in FIG. 2. In the other configuration, in which the inlet valve member 35 closes the inlet 59 and the outlet valve member 36 has opened the outlet 70, the link 73 occupies the position shown in phantom.

The link 73, moving between the two shown positions, propels the valving members 35 and 36 to their proper orientation. There, they control the casette 27 during the different portions of the operating cycle.

The link 73 has sufficient springiness or resiliency to close the open valve before it allows the closed valve to open. Thus, during no time can the inlet 59 and the outlet 70 simultaneously remain open and allow the uncontrolled flow of fluid to the patient. At all times, the spring link 73 causes one of these valves to occupy its closed position.

As FIGS. 2 and 3 show, the spring link 73 has the legs 74 which couple to the rocker-arm armature 75 of the electromagnet 45. The rivets 76 attaches the two together while the tabs 77 on the arms 74 assure that the spring link 73 pivots as the rocker arm 75 changes its positions.

In addition to the rocker arm 75, the electromagnet 47 includes the E-frame 80. Around the middle leg 81 of the E-frame 80 appears the coil 83 which receives current along the leads 84. Current flowing along the leads 84 causes the ends 87 and 88 of the side legs 89 and 90, respectively, of the E-frame 80 to become magnetic poles of the same type. For example, current flowing in one direction in the leads 84 may cause the ends 87 and 88 to both become North magnetic poles.

However, the rocker arm 75 itself constitutes a permanent magnet. Thus, for example, one of its ends 93 may have the South magnetic pole while the other end 94 has the North magnetic pole. With the current in the leads 84 producing North magnetic poles at the ends 87 and 88, the South pole of the rocker arm end 93 will feel an attraction to the end 87 of the side leg 89. Concurrently, the North pole at the rocker arm end 94 will undergo a repulsion from the North magnetic pole at the end 88 of the side leg 90. These combined poles would force the rocker arm 75 to pivot about the point 95 into the position shown by the solid lines of FIG. 2.

Reversing the direction of the current in the leads 84 would produce the opposite effect. The current flowing in the second direction will produce South magnetic poles at the ends 87 and 88 of the side legs 89 and 90, respectively. The South magnetic pole at the end 87 will repel the South pole at the rocker arm end 93. Simultaneously, the South pole at the end 88 of the bottom side leg 90 will attract the North pole at the end 94 of the rocker arm 75. This will cause the rocker arm 75 to pivot from the position shown in solid lines of FIG. 2 to the position shown in phantom there.

As the rocker arm 75 pivots between these two positions, the spring link 73 pivots between its two illustrated positions. As it does, it changes the positions of the inlet and outlet valve members 35 and 36.

When the spring link 73 occupies the position shown in solid lines in FIG. 2, the inlet valve member 35 opens the inlet 58. Further, the outlet valve member 36 closes the outlet 70. When the link 73 occupies the position shown in phantom, the inlet valve member 35 closes the inlet 58 while the outlet valve member 36 opens the outlet 70. Thus, to operate the casette 27, the controller provides current along the leads 84 in the proper direction to move the rocker arm between the two positions which alternately opens and closes the inlet 59 and the outlet 70.

The current in the leads 84 need remain on only sufficiently long to move the rocker arm 75 between the two shown positions. The current can stop during the times that the rocker arm 75 remains in one of its two positions. During that time, the magnetic pole of the rocker arm 75 in contact with the E-frame 80 will exert an attraction to the ferromagnetic material of the E-frame 80. The magnetic pole at the other end of the rocker arm will do so likewise. However, lying further away, it has considerably less attraction for the ferromagnetic material of the E-frame 80. Thus, the rocker arm 75, in the absence of current in the leads 84, constitutes a bistable magnetic device. It consequently remains in the position which the current passing through the leads 84 and the coil 83 has placed it.

As FIGS. 2 and 3 show, the rocker arm 75 includes a strip of plastic 97 lying between it and the middle leg 81 of the E-frame 80. As its primary function, the plastic strip 97 separates the material of the permanent magnet 75 from the E-frame's middle leg 81. If these two components could make contact with each other, they could create a magnetic shunt across the middle leg 81. This would reduce the forces operating between the poles of the permanent magnet rocker-arm armature 75 and the side legs 87 or 88 of the E-frame 80. With a permanent magnet 75, the development of such a shunt represents a minor problem since the middle section of a permanent magnet does not, itself, readily magnitize. However, a rocker arm having two separate permanent magnets at its ends could function as the armature. In this case, the contact between the middle leg 81 and the rocker arm could produce an appreciable shunting of the magnetic field across the connection between the rocker arm and the middle leg 81. Separating the two components prevents the development of this shunting.

The space between the rocker arm 75 and the middle leg 81 need not have the plastic material 97 filling it. An air gap between the two components would work as effectively. However, placing the plastic strip 97 between them allows for mechanical contact between the components to increase the strength and rigidity of the coupling of the rocker arm 75 to the E-frame 80.

Furthermore, the plastic strip 97 keeps the rocker arm 75 from grinding against the middle leg 81. Accordingly, the frictional resistance of the motion of the former as it moves decreases. This helps minimize the current required to operate the controller. Moreover, should the metallic material of the rocker arm grind against the ferromagnetic material of the middle leg 81, they could produce filings between them. These filings could further increase the rocker arm's resistance to motion.

The strip of plastic 97 may take the form of Mylar ® (sold by the E. I. duPont de Nemours & Co. of Wilmington, Del.), having an adhesive backing. This allows for its direct application to the rocker arm 75. Mylar ® with adhesive backing is sold by the 3M Co., St. Paul, Minn.

The rocker arm 75 rotates about the pivot point 95 in FIGS. 2 and 3. Placing the pivot point closer to the rocker arm itself would portend the possibility of the controller 10 operating with greater efficiency. FIG. 4 shows a middle leg 98 of an E-frame magnet having a pivot point 99 at its end. The rocker arm 75 pivots about that point 99 which actually contacts the rocker arm 75. The coupling 100 must provide some freedom of motion in order to allow the rocker arm 75 to pivot about the point 99. Also as shown in FIG. 4, the strip of Mylar ® 101 attaches to the middle leg 98 rather than the rocker arm 75.

Accordingly, what is claimed is:
1. In a controller for use with a casette having:
   (1) metering means for holding a predetermined volume of a fluid;
   (2) closable inlet means, in fluid communication with said metering means, for permitting the flow of a fluid into said metering means; and
   (3) closable outlet means, in fluid communication with said metering means, for permitting the flow of a fluid out of said metering means;
said controller having:
   (A) first rigid member means movable between a first position and a second position, for when in said second position, closing said inlet means;
   (B) second rigid member means, movable between a third position and a fourth position, for, when in said fourth position, closing said outlet means; and
   (C) actuating means, commentable to and operatable on a source of power, for selectively and alternatively moving said first member means to said second position to close said inlet means and moving said second member means to said fourth position to close said outlet means, said actuating means including bistable magnetic means for, in the absence of power for said actuating means, moving said first member into said second position or moving said second member into said fourth position, the improvement wherein said bistable magnetic means includes a single permanent magnet defining an elongated rigid member having its magnetic poles in the vicinity of the ends of said elongated member, and electromagnet means having magnetic poles, said poles of the permanent magnet being located in proximity to a pole of said electromagnet means, and pivoting means to permit said permanent magnet to pivotally move responsive to the polarity of said electromagnet pole, said permanent magnet having an arcuate shape with said permanent magnetic poles having their strongest field strengths oriented at least partly toward said electromagnet poles.

2. The improvement of claim 1 wherein said electromagnet is an E-frame electromagnet with a first electromagnetic pole being on one side leg of said E-frame and a second electromagnetic pole being on the other side leg on said E-frame with a coil surrounding said middle leg of said E-frame, and wherein said rocker arm pivots about a point lying on a line passing lengthwise through said middle leg.

3. The improvement of claim 2 wherein said actuating means includes structural means, coupled to said rocker arm or to said E-frame, for maintaining said rocker arm spatially removed from said middle leg of said E-frame.

4. The improvement of claim 3 wherein said power means selectively provides current to said coil on the middle leg of said E-frame in a first direction to move said first member means into said second position and in a second direction opposite to said first direction to move said second member means into said fourth position.

5. The improvement of claim 4 wherein said coil is formed from approximately 2072 turns of No. 33 copper wire with a polyurethane coating.

6. In a fluid-flow limiting combination having:
   (A) a casette with:
      (1) metering means for holding a predetermined volume of fluid;
      (2) closable inlet means, in fluid communication with said metering means, for permitting the flow of a fluid into said metering means; and
      (3) closable outlet means, in fluid communication with said metering means, for permitting the flow of a fluid out of said metering means;
   (B) a controller with:
      (1) first rigid member means, movable between a first position and a second position, for, when in said second position, closing said inlet means;
      (2) second rigid member means, movable between a third position and a fourth position for closing said outlet means; and
      (3) actuating means, connectable to and operatable on a source of power, for selectively and alternatingly moving said first member means to said second position to close said inlet means and moving said second member means to said fourth position to close said outlet means, said actuating means including bistable magnetic means for, in the absence of power for said actuating means, moving said first member means into said second position and moving said second member means into said fourth position;

the improvement wherein said bistable magnetic means includes a single permanent magnet defining an elongated rigid member having its magnetic poles in the vicinity of the ends of said elongated member, an electromagnet, said poles being located in proximity to a pole of said electromagnet, said permanent magnet being pivotably movable in response to the polarity of said electromagnet pole, said permanent magnet defining an arcuate shape with its poles having their strongest field strength oriented at least partially toward said electromagnet pole.

7. The improvement of claim 6 wherein said electromagnet is an E-frame electromagnet with said first electromagnetic pole being on one side leg of said E-frame and said second electromagnetic pole being on the other side leg on said E-frame with a coil surrounding said middle leg of said E-frame, and wherein said rocker arm pivots about a point lying on a line passing lengthwise through said middle leg.

8. The improvement of claim 7 wherein said rocker arm and said first and second magnetic poles constitute a permanent magnet in the form of an elongated rigid member having its magnetic poles in the vicinity of the ends of said elongated member.

9. The improvement of claim 8 wherein the space between the rocker arm and said middle leg of the E-frame is substantially filled with a plastic material having a low coefficient of friction.

10. In a controller for use with a casette having:
(1) metering means for holding a predetermined volume of a fluid;
(2) closable inlet means, in fluid communication with said metering means, for permitting the flow of a fluid into said metering means; and
(3) closable outlet means, in fluid communication with said metering means, for permitting the flow of a fluid out of said metering means;
said controller having:
(1) first rigid member means, movable between a first position and a second position, for when in said second position, closing said inlet means;
(2) second rigid member means, movable between a third position and a fourth position, for, when in said fourth position, closing said outlet means; and
(3) magnetic actuating means, connectable to and operatable on a source of electric current, for selectively and alternatingly moving said first member means to said second position to close said inlet means and moving said second member means to said fourth position to close said outlet means,
the improvement wherein said actuating means includes:
(A) a single permanent magnet, coupled to said first and second member means, in the form of an elongated rigid member having its magnetic poles in the vicinity of the ends of said elongated member; and
(B) an electromagnet having electromagnetic poles located in proximity to said poles of said permanent magnet, said electromagnet including a coil connectable to said source of electric current and selectively inducing said poles of said electromagnet to both become magnetic poles of a first type or to both become magnetic poles of a second type, said permanent magnet being pivotable, relative to said electromagnet, at a location located on a first line which perpendicularly bisects a second line extending between said magnetic poles of said permanent magnet, said permanent magnet having an arcuate shape and having magnetic poles in which their strongest field strength is oriented at least partially toward said electromagnet.

11. In a controller for use with a casette having:
(1) metering means for holding a predetermined volume of a fluid;
(2) closable inlet means, in fluid communication with said metering means, for permitting the flow of a fluid into said metering means; and
(3) closable outlet means, in fluid communication with said metering means, for permitting the flow of a fluid out of said metering means;
said controller having:
(a) first rigid member means, movable between a first position and a second position, for, when in said second position, closing said inlet means;
(b) second rigid member means, movable between a third position and a fourth position, for, when in said fourth position, closing said outlet means; and
(c) magnetic actuating means, connectable to and operatable on a source of electric current, for selectively moving said first member means to said second position to close said inlet means and said second member means to said fourth position to close said outlet means, said actuating means including (i) an E-frame electromagnet having a coil connectable to said source of electric current and wrapped around the middle leg of said E-frame and (ii) a rigid rocker arm comparising permanent magnet means having first and second magnetic poles, said rocker arm being located in proximity to said E-frame and pivotable between first and second positions about a point located on a first line which perpendicularly bisects a second line extended between said first and second magnetic poles, said second line passing through, in a lengthwise direction, said middle leg of said E-frame, said rocker arm, in said first position, placing said first magnetic pole in the vicinity of one side leg of said E-frame and said second magnetic pole away from the other side leg of said E-frame, and, in said second position, said second magnetic pole in the vicinity of the other side leg of said E-frame and said first magnetic pole away from said one side leg of said E-frame, the improvement wherein said actuating means includes structural means, coupled between said rocker arm and said E-frame for maintaining said rocker arm spatially removed from said middle leg of said E-frame, the space between said rocker arm and the middle leg of said E-frame being substantially filled with an insulating plastic material having a low coefficient of friction.

12. A fluid-flow combination having:
(a) a casette with:
(1) metering means for holding a predetermined volume of fluid;
(2) closable inlet means, in fluid communication with said metering means, for permitting the flow of a fluid into said metering means;
(3) closable outlet means, in fluid communication with said metering means, for permitting the flow of a fluid out of said metering means;
(b) a controller with:

(1) first rigid member means, movable between a first position and a second position, for when in said second position, closing said inlet means;
(2) second rigid member means, movable between a third position and a fourth position, for when in said fourth position, closing said outlet means;
(3) magnetic actuating means, connectable to and operatable on a source of electric current, for selectively moving said first member means to said second position to close said inlet means and said second means to said fourth position to close said outlet means; said actuating means including (i) an E-frame electromagnet having a coil connectable to said source of electric current and wrapped around the middle leg of said E-frame and (ii) a rigid rocker arm comprising permanent magnet means having first and second magnetic poles, said rocker arm being located in proximity to said E-frame and pivotable between first and second positions about a point located on a first line which perpendicularly bisects a second line extended between said first and second magnetic poles, said second line passing through, in a lengthwise direction, said middle leg of said E-frame, said rocker arm, in said first position, placing said first magnetic pole in the vicinity of one side leg of said E-frame and said second magnetic pole away from the other side leg of said E-frame and, in said second position, said second magnetic pole in the vicinity of the other side leg of said E-frame, and said first magnetic pole away from said one side of said E-frame leg, the improvement wherein said actuating means includes structural means, coupled between said rocker arm and said E-frame for maintaining said rocker arm spatially removed from said middle leg of said E-frame, the space between the rocker arm and said middle leg of the E-frame containing an insulating plastic material having a low coefficient of friction.

* * * * *